United States Patent [19]
Agostini et al.

[11] Patent Number: 6,024,969
[45] Date of Patent: Feb. 15, 2000

[54] COSMETIC/DERMATOLOGICAL COMPOSITIONS FORMULATED AS SUPPLE DOUGHS

[75] Inventors: Isabelle Agostini, Chatenay Malabry; Dolorès Miguel-Colombel, L'Hay-les-Roses; François Pradier, Fontenay aux Roses; Alex Junino, Livry Gargan; Veronique le Bras-Roulier, Paris, all of France

[73] Assignee: Societe l'Oreal S.A., Paris, France

[21] Appl. No.: 08/690,643

[22] Filed: Jul. 29, 1996

[51] Int. Cl.[7] ..................................................... A61K 7/027
[52] U.S. Cl. ................................ 424/401; 424/63; 424/59
[58] Field of Search ................................ 424/401, 63, 59

[56] References Cited

U.S. PATENT DOCUMENTS 5,061,481  10/1991  Suzuki et al. ............................ 424/63

Primary Examiner—Keith D. MacMillan
Assistant Examiner—D. Faulkner
Attorney, Agent, or Firm—Burns, Doane, Swecker & Mathis, L.L.P.

[57] ABSTRACT

Transfer-resistant cosmetic/dermatological compositions (e.g., lipcolors) formulated as supple and homogeneous doughs, advantageously via extrusion, include a fatty phase which comprises at least one volatile oil, at least one phenylated silicone oil and at least 12% by weight of at least one wax.

31 Claims, No Drawings

COSMETIC/DERMATOLOGICAL COMPOSITIONS FORMULATED AS SUPPLE DOUGHS

CROSS-REFERENCE TO COMPANION APPLICATIONS

Copending applications Ser. No. 08/687,996 [Attorney Docket No. 016800-105] and Ser. No. 08/688,027 [Attorney Docket No. 016800-106], each filed concurrently herewith, and each assigned to the assignee hereof.

BACKGROUND OF THE INVENTION

1. Technical Field of the Invention

The present invention relates to novel compositions, notably for topical cosmetic applications, formulated as supple doughs which are useful for the care and/or makeup of the lips and/or of the skin.

2. Description of the Prior Art

Cosmetic compositions known to this art which can be topically applied to the skin or the lips as a makeup or care product, such as, for example, the bases for lips or lipsticks, generally contain fatty substances including waxes, pigments and/or fillers and, optionally, adjuvants and additives. It is known that the greater the amount of waxes which is present in the composition, the firmer the consistency of the latter, and this permits same to be used in stick form.

However, the formulation, in particular of a colored lip makeup, in stick form presents certain disadvantages: the drawing of the lip outlines is not very easy and the heat resistance of the stick is not the optimum.

There are also known cosmetic compositions which are in the form of a supple dough that can be applied with the aid of a brush, for example. These compositions generally contain no or little wax, especially in a minor amount on the order of 8%–12%, and which enables them to be picked up and applied with ease, since a larger amount of waxes would provide a composition of higher viscosity which then could not be applied.

However, the waxes permit certain advantageous properties to be imparted to such compositions, in particular smoothness and film resistance and thickness.

Furthermore, it too has been found that the compositions of the prior art exhibit the disadvantage of transfer, namely, of being transferred at least partially, leaving a mark, on certain substrates with which they are contacted, especially a glass, a garment or the skin. This results in a mediocre persistence of the film on the lips, making it necessary to reapply the colored lip makeup composition at regular intervals.

SUMMARY OF THE INVENTION

Accordingly, a major object of the present invention is the provision of novel cosmetic/dermatological compositions formulated as supple doughs, which contain a large amount of waxes in comparison with counterpart compositions of the prior art, but which exhibit reduced transfer properties.

Briefly, the present invention features novel compositions which are formulated as supple doughs and which comprise, in a fatty phase thereof, a volatile oil, a phenylated silicone oil and at least 12% by weight of wax.

This invention also features a process for the formulation of the subject compositions, comprising preparing a premix including at least a proportion of the various constituents of the composition, which comprises at least the wax or waxes, next heating this premix to a temperature at which it melts, if appropriate, adding the remaining constituents while the mixture obtained is being blended, and then cooling the mixture obtained while being blended during at least a part of its cooling cycle, the blending being carried out at least in part in a mixer/extruder.

The present invention also features formulating the combination of a volatile oil and of a phenylated silicone oil into compositions comprising at least 12% by weight of wax in order to decrease the transfer and/or the migration of said compositions and/or in order to improve the behavior thereof.

DETAILED DESCRIPTION OF BEST MODE AND SPECIFIC/PREFERRED EMBODIMENTS OF THE INVENTION

More particularly according to the present invention, the subject compositions are supple doughs whose viscosity can be measured, in contrast to the solid structure of a rod or stick, the viscosity of which cannot be measured. Their dynamic viscosity at 25° C. generally ranges from 3 to 35 Pa.s, measured using a Contraves TV rotary viscometer fitted with an "MS-r4" rotor at a frequency of 60 Hz.

It has also determined that the films obtained from the compositions according to the invention behave well and do not present any migration problem. Such films do not, indeed, exhibit any tendency to propagate within the small wrinkles of the skin which surround the lips, producing an unaesthetic effect.

The compositions according to the invention therefore include a fatty phase comprising at least one wax, at least one volatile oil and at least one phenylated silicone oil are present.

The wax constituting a fraction of the subject compositions preferably has a melting point higher than approximately 45° C. and in particular higher than 55° C. and/or a needle penetration number at 25° C. which preferably ranges from 3 to 40.

Exemplary such waxes, employed either alone or in admixture, include animal, vegetable, mineral and synthetic waxes such as beeswax, carnauba, candelilla, ouricury and Japan wax, cork fiber or sugarcane waxes, paraffin and lignite waxes, microcrystalline waxes, ozokerites, polyethylene waxes and the waxes obtained via Fischer-Tropsch synthesis, and silicone waxes.

The subject compositions preferably include 15%–60% by weight of waxes which have a melting point higher than 55° C.

Thus, since the compositions according to the invention have a high wax content, greater than 12% by weight, they form a film which behaves well when applied as a layer, especially on the lips.

The compositions of this invention also include a volatile oil which may be selected, in particular, from among the hydrocarbon oils or cyclic or linear silicone oils, whether alone or mixed.

By "volatile oil" is intended any oil capable of evaporating on contact with the skin. Oils whose flash point is sufficiently high to permit the use thereof in a given formulation, and sufficiently low to obtain the desired evanescent effect, are preferably employed. Oils whose flash point is on the order of 40°–100° C. are more preferably employed. Exemplary volatile silicone oils include cyclotetradimethylsiloxane, cyclopentadimethylsiloxane, cyclohexadimethylsiloxane and methylhexyldimethylsiloxane. Isoparaffins are representative of the volatile hydrocarbon oils.

The compositions of the present invention may include 8%–70% by weight, preferably 30%–60%, of volatile oils, relative to the total weight of the composition.

The compositions of the invention also include at least one phenylated silicone oil.

This oil may be a polyphenylmethylsiloxane or a phenyltrimethicone, or a mixture of different phenylated silicone oils and in particular may have the following structural formula (I):

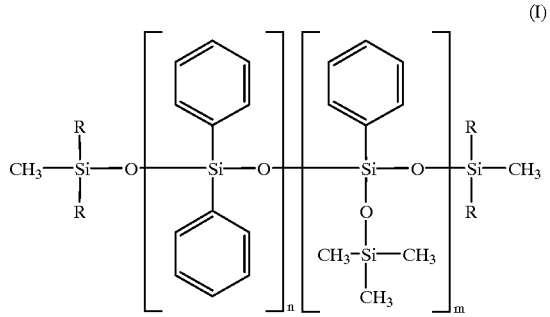

in which R is a $C_1$–$C_{30}$ alkyl radical, an aryl radical or an aralkyl radical; n is an integer ranging from 0 to 100; and m is an integer ranging from 0 to 100, with the proviso that the sum m+n ranges from 1 to 100.

R is preferably a methyl, ethyl, propyl, isopropyl, decyl, dodecyl or octadecyl radical, or a phenyl, tolyl, benzyl or phenethyl radical.

Exemplary of these phenylated oils are the Belsil PDM1000 oil marketed by Wacker, the DC556 or SF558 oils marketed by Dow Corning, the Abil AV8853 oil marketed by Goldschmidt and the Silbione 70633V30 oil marketed by Rhône Poulenc.

The compositions according to the invention may include 1%–35% by weight, preferably 10%–20%, of phenylated silicone oils.

In addition to those constituents indicated above, the subject compositions may also comprise other fatty substances conventional in this art, and especially oils, gums and/or pasty fatty substances of vegetable, mineral, animal, synthetic or silicone origin.

Exemplary such silicone fatty substances include polydimethylsiloxanes (PDMS) and alkyldimethicones, as well as the silicones modified with aliphatic and/or aromatic substituents, optionally fluorinated, or with functional groups such as hydroxyl, thiol and/or amine groups.

Exemplary nonsilicone fatty substances include liquid paraffin, liquid petrolatum, perhydrosqualene, arara, sweet almond, calophyllum, palm, castor, avocado, jojoba, olive or wheat germ oil, fatty acid esters, alcohols, acetylglycerides, alcohol or polyalcohol octanoates, decanoates or ricinoleates, fatty acid triglycerides, glycerides, hydrogenated oils which are solid at 25° C., lanolins and fatty esters which are solid at 25° C.

These fatty substances may in particular be variously selected by one skilled in this art in order to formulate a composition which has the desired properties, for example in respect of consistency or texture.

However, preferably, the compositions of the invention comprise less than 20% by weight of nonvolatile hydrocarbon oil and, for example, less than 5% by weight, or even none at all. Indeed, it has been determined that in this case the "nontransfer" properties of the subject compositions obtained are further improved.

The subject compositions may also include a particulate phase, generally present in a proportion of 0%–35% by weight, preferably 5%–25% by weight, and which may comprise pigments and/or "mothers-of-pearl" and/or fillers which are typically employed in cosmetic compositions.

The pigments may be present in the composition in a proportion of 0%–30% by weight of the final composition, and preferably in a proportion of 10%–15%. They may be white or colored, inorganic and/or organic. Exemplary inorganic pigments include titanium, zirconium or cerium dioxides and zinc, iron or chromium oxides and ferric blue. And exemplary organic pigments include carbon black and barium, strontium, calcium and aluminum lacquers. The mothers-of-pearl may be present in the composition in a proportion of 0%–20% by weight, preferably in a high ratio on the order of 8%–15% by weight. Exemplary mothers-of-pearl include mica coated with titanium dioxide, with iron oxide, with natural pigment or with bismuth oxychloride, and colored titanium mica.

The fillers, which may be present in a proportion of 0%–30% by weight, preferably 5%–15%, in the subject compositions, may be inorganic or synthetic, lamellar or nonlamellar. Representative thereof are talc, mica, silica, kaolin, nylon and polyethylene powders, Teflon, starch, micatitanium, natural mother-of-pearl, boron nitride, microspheres such as Expancel (Nobel Industrie), polytrap (Dow Corning) and silicone resin microbeads (for example Tospearls marketed by Toshiba).

The subject compositions may additionally contain any additive or adjuvant usually employed in the cosmetic field, such as antioxidants, perfumes, essential oils, preservatives, cosmetic active substances, hydrating or moisturizing agents, vitamins, essential fatty acids, sphingoceryls, artificial suntanning agents such as DHA, sunscreens, surfactants, liposoluble, especially hydrocarbon, polymers such as polybutene, polyalkylenes, polyacrylates and silicone polymers which are compatible with the fatty substances.

One skilled in this art will obviously take care to select the possible additional compounds and/or their quantity, in such manner that the advantageous properties of the compositions according to the invention are not, or substantially are not, compromised by the intended addition.

The compositions of the invention may be formulated in the following manner. A premix is first prepared including at least a proportion of the various constituents of the composition, including at least the wax or waxes. This premix is heated to a temperature at which it melts, if appropriate the remaining constituents being added thereto while the mixture obtained is being blended. Then the mixture obtained is cooled, while being blended during at least a part of the cooling cycle, the blending being carried out at least partially in a mixer/extruder.

The cooling is preferably down to ambient temperature, at which temperature the volatile oil may be added. However, the volatile oil may also be added during the cooling stage, preferably at a temperature which is lower than or equal to approximately 45° C.

This process permits the formulation of compositions which are in the form of supple and homogeneous doughs, even though they contain waxes and optionally a particulate phase, in a large amount.

In addition, such doughs are of uniform and reproducible quality.

The heating operation may be carried out via any known technique.

In a preferred embodiment of the invention, the heating and blending, or even cooling, operations are carried out entirely in one or several mono- or twin-screw extruders arranged in series, and preferably in a single twin-screw extruder.

Too, by adapting the outlet die of the mixer/extruder, it is possible to package the composition in-line at the exit of said mixer/extruder.

It has been determined that the subject compositions obtained after extrusion exhibit an especial softness and provide a certain sliding sensation when topically applied to the skin, while at the same time avoiding the appearance and the sensation of oily grease. The conditions under which the extrusion may be carried out are described in FR-94/00,756, hereby expressly incorporated by reference.

The compositions according to this invention may be presented in the form of a cosmetic composition and, especially, may be formulated as a makeup product for the skin, in particular a foundation, a blusher or an eyeshadow, or a colored lip makeup. They may also be presented in colorless form, optionally containing cosmetic active agents. They may then particularly be employed as a base for lip care or as a fixative or fixing base to be applied over a conventional colored lip makeup. The fixing base then forms a protective film over the film of colored makeup, limits its transfer and migration, and, thus, enables its durability to be increased.

The compositions may also be presented in the form of a dermatological or skin care preparation, or else in the form of a sun, sunscreen or artificial suntan preparation.

In order to further illustrate the present invention and the advantages thereof, the following specific examples are given, it being understood that same are intended only as illustrative and in nowise limitative.

EXAMPLE 1:
A colored lip makeup was formulated as a supple dough having the following composition:

| | | |
|---|---|---|
| (a) | cyclopentadimethylsiloxane | 40 g |
| (b) | polyphenylmethylsiloxane (DC556 fluid marketed by Dow Corning) | 15 g |
| (c) | pasty silicone fatty substance | 5 g |
| (d) | waxes (silicone and polyethylene) | 25 g |
| (e) | pigments | 10 g |
| (f) | fillers | 5 g |

These various ingredients, with the exception of the volatile oil, were introduced into a twin-screw extruder at an inlet temperature of approximately 75°–95° C.

The volatile oil was introduced into the extruder at the end of extrusion, at a temperature on the order of 20°–25° C.

At the outlet, a supple dough having a viscosity of 27 Pa.s was obtained, which was in the form of a stable and homogeneous single phase and could be picked up with the aid of a brush for its application.

This composition could be converted into a homogeneous film which was easily applied and which spread easily and uniformly. The film obtained also had a light texture and remained comfortable to wear all day long.

This composition was applied to the left portions of the lips of several test subjects.

For purposes of comparison, a colored lip makeup was applied to the right portions of said lips, in the form of a conventional supple dough, including neither volatile silicone oil nor phenylated silicone oil.

The colored lip makeups were permitted to dry at ambient temperature for 5 minutes and then the entire lips were blotted with a sheet of paper.

On all sheets of paper a large red mark resulted, which was transferred thereto by the composition according to the prior art.

The composition according to the invention transferred a very weak, barely perceptible mark onto each sheet.

EXAMPLE 2:
A fixing base for colored lip makeup was prepared in the form of supple dough, which had the following composition:

| | | |
|---|---|---|
| (a) | cyclopentadimethylsiloxane | 40 g |
| (b) | polyphenylmethylsiloxane (DC556 fluid marketed by Dow Corning) | 15 g |
| (c) | silicone pasty fatty substance | 5 g |
| (d) | waxes (silicone and polyethylene) | 25 g |
| (e) | fillers | 15 g |

The preparation was carried out according to the procedure of Example 1.

The film obtained by application of the composition was homogeneous and could be applied with ease, spreading easily and uniformly over a conventional colored lip makeup.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A cosmetic/dermatological composition formulated as a supple and homogeneous dough including a fatty phase, said fatty phase comprising at least one volatile oil, at least one phenylated silicone oil and at least 12% by weight of at least one wax.

2. The cosmetic/dermatological composition as defined by claim 1, said at least one volatile oil comprising a hydrocarbon oil, or a cyclic or linear silicone oil, or combination thereof.

3. The cosmetic/dermatological composition as defined by claim 2, said at least one volatile oil comprising cyclotetradimethylsiloxane, cyclopentadimethylsiloxane, cyclohexadimethylsiloxane, methylhexyldimethylsiloxane or an isoparaffin, or combination thereof.

4. The cosmetic/dermatological composition as defined by claim 1, said at least one volatile oil comprising from 8% to 70% by weight thereof.

5. The cosmetic/dermatological composition as defined by claim 1, said at least one phenylated silicone oil having the structural formula (I):

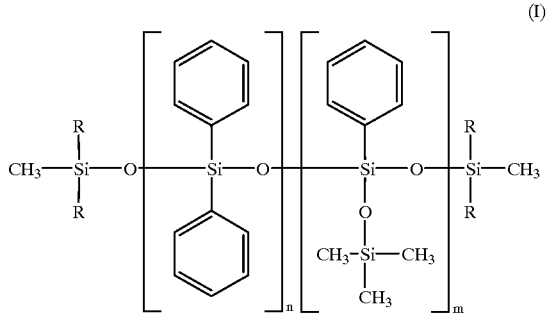

in which R is a $C_1$–$C_{30}$ alkyl radical, an aryl radical or an aralkyl radical; n is an integer ranging from 0 to 100; and m is an integer ranging from 0 to 100, with the proviso that the sum m+n ranges from 1 to 100.

6. The cosmetic/dermatological composition as defined by claim 5, wherein formula (I), R is a methyl, ethyl, propyl, isopropyl, decyl, dodecyl, octadecyl, phenyl, tolyl, benzyl or phenethyl radical.

7. The cosmetic/dermatological composition as defined by claim 1, said at least one phenylated silicone oil comprising from 1% to 35% by weight thereof.

8. The cosmetic/dermatological composition as defined by claim 1, said at least one wax having a melting point higher than approximately 45° C. and/or a needle penetration number, at 25° C., ranging from 3 to 40.

9. The cosmetic/dermatological composition as defined by claim 1, said at least one wax comprising an animal, vegetable, mineral or synthetic wax.

10. The cosmetic/dermatological composition as defined by claim 9, said at least one wax comprising beeswax, carnauba, candelilla, ouricury or Japan wax, cork fiber or a sugarcane wax, a paraffin or lignite wax, a microcrystalline wax, an ozokerite, a polyethylene wax, a wax obtained via Fischer-Tropsch synthesis, a silicone wax, or combination thereof.

11. The cosmetic/dermatological composition as defined by claim 1, said at least one wax comprising from 15% to 60% by weight thereof.

12. The cosmetic/dermatological composition as defined by claim 1, comprising more than 0% but less than 20% by weight of a nonvolatile hydrocarbon oil.

13. The cosmetic/dermatological composition as defined by claim 1, comprising up to 35% by weight of a particulate phase.

14. The cosmetic/dermatological composition as defined by claim 1, further comprising a cosmetically or dermatologically acceptable carrier, diluent or vehicle therefor.

15. The cosmetic/dermatological composition as defined by claim 4, said at least one volatile oil comprising from 30% to 60% by weight thereof.

16. The cosmetic/dermatological composition as defined by claim 7, said at least one phenylated silicone oil comprising from 10% to 20% by weight thereof.

17. The cosmetic/dermatological composition as defined by claim 8, said at least one wax having a melting point higher than 55°.

18. The cosmetic/dermatological composition as defined by claim 12, comprising less than 5% by weight of said nonvolatile hydrocarbon oil.

19. The cosmetic/dermatological composition as defined by claim 13, comprising from 5% to 25% by weight of said particulate phase.

20. The cosmetic/dermatological composition as defined by claim 1, comprising a preparation for the care and/or makeup of the lips and/or of the skin.

21. The cosmetic/dermatological composition as defined by claim 20, comprising a lipcolor, foundation, blusher, or an eyeshadow.

22. The cosmetic/dermatological composition as defined by claim 20, comprising a sunscreen or artificial suntanning preparation.

23. The cosmetic/dermatological composition as defined by claim 20, comprising a fixative for a lip preparation.

24. A process for the formulation of the cosmetic/dermatological composition as defined by claim 1, comprising preparing a premix including at least a fraction of the various constituents thereof and which comprises said at least one wax, next heating said premix to the melting point thereof while, if appropriate, adding the remaining constituents thereto and, at the same time, blending said premix, and then cooling the mixture obtained, said blending being carried out at least in part during said cooling step and at least in part in a mixer-extruder.

25. The process as defined by claim 24, comprising adding said at least one volatile oil to the blended mixture during said cooling step.

26. The process as defined by claim 24, comprising heating and cooling in one, or a plurality of extruders arranged in series.

27. The process as defined by claim 26, comprising heating, blending and cooling in a single twin-screw extruder.

28. The cosmetic/dermatological composition as defined by claim 1, which is anhydrous.

29. The cosmetic/dermatological composition as defined by claim 1, which is produced by a process including at least one step which comprises blending a melt constituent which includes at least a fraction of the constituents of the composition of claim 1, and which comprises at least one wax, while cooling said melt constituent.

30. The cosmetic/dermatological composition of claim 29, wherein said blending is effected at least in part in a mixer/extruder.

31. A cosmetic/dermatological composition produced by the process of claim 24.

* * * * *